United States Patent [19]

Horn et al.

[11] Patent Number: 5,087,247
[45] Date of Patent: Feb. 11, 1992

[54] BALLOON PERFUSION CATHETER

[75] Inventors: Joseph B. Horn, Topsfield, Mass.; Allen J. Tower, North Lawrence, N.Y.; James F. King, Wauwatosa, Wis.

[73] Assignee: Cardiovascular Designs, Inc., Peabody, Mass.

[21] Appl. No.: 574,370

[22] Filed: Aug. 28, 1990

[51] Int. Cl.⁵ .................................... A61M 29/00
[52] U.S. Cl. ...................... 604/98; 604/96; 606/192; 606/194
[58] Field of Search .................. 128/207.15; 604/96–103, 53; 606/191–194; 600/31, 32

[56] References Cited

U.S. PATENT DOCUMENTS

| | | | |
|---|---|---|---|
| 3,087,493 | 4/1963 | Schossow | 128/207.15 |
| 3,428,046 | 2/1969 | Remer et al. | |
| 3,693,624 | 9/1972 | Shiley et al. | 128/207.15 |
| 3,731,692 | 5/1973 | Goodyear | 128/207.15 |
| 3,908,664 | 9/1975 | Loseff | |
| 4,214,593 | 7/1980 | Imbruce et al. | |
| 4,385,631 | 5/1983 | Uthmann | 604/53 |
| 4,423,725 | 1/1984 | Baran et al. | |
| 4,471,776 | 9/1984 | Cox | 128/207.15 |
| 4,545,390 | 10/1985 | Leary | |
| 4,581,017 | 4/1986 | Sahota | |
| 4,661,094 | 4/1987 | Simpson | 604/53 |
| 4,674,495 | 6/1987 | Orr | 128/207.15 |
| 4,689,041 | 8/1987 | Corday et al. | 604/96 |
| 4,751,924 | 6/1988 | Hammerschmidt et al. | 128/207.15 |
| 4,771,777 | 9/1988 | Horzewski et al. | |
| 4,790,315 | 12/1988 | Mueller, Jr. et al. | |
| 4,800,901 | 1/1989 | Rosenberg | 606/192 |
| 4,850,969 | 7/1989 | Jackson | |
| 4,857,054 | 8/1989 | Helfer | |
| 4,917,088 | 4/1990 | Crittenden | |

FOREIGN PATENT DOCUMENTS 1102-610-A 7/1984 U.S.S.R.

Primary Examiner—C. Fred Rosenbaum
Assistant Examiner—Chalin Smith
Attorney, Agent, or Firm—Peter F. Corless; Gregory D. Williams

[57] ABSTRACT

Balloon perfusion catheter having a flexible elongated shaft from which a perfusion shaft and an inflation shaft outwardly extend. An angioplasty balloon is circumferentially mounted around the perfusion shaft. The inflation shaft distal end is located at the balloon proximal end. Openings in the perfusion shaft both proximal and distal to the balloon permit blood flow through artery during balloon inflation.

17 Claims, 1 Drawing Sheet

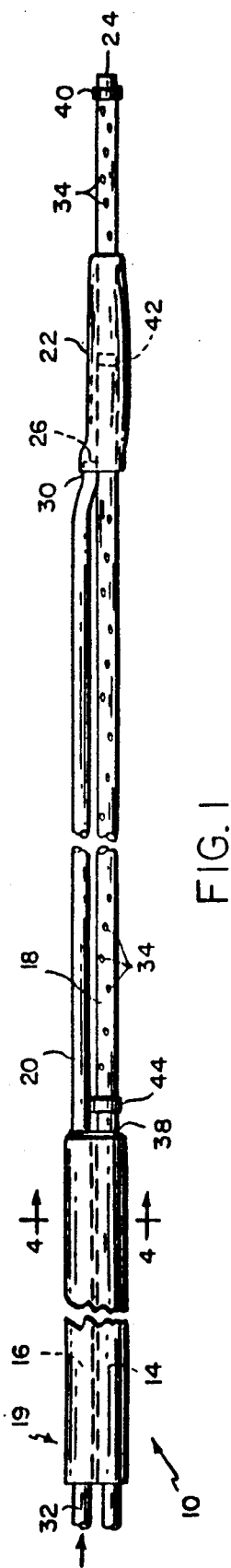
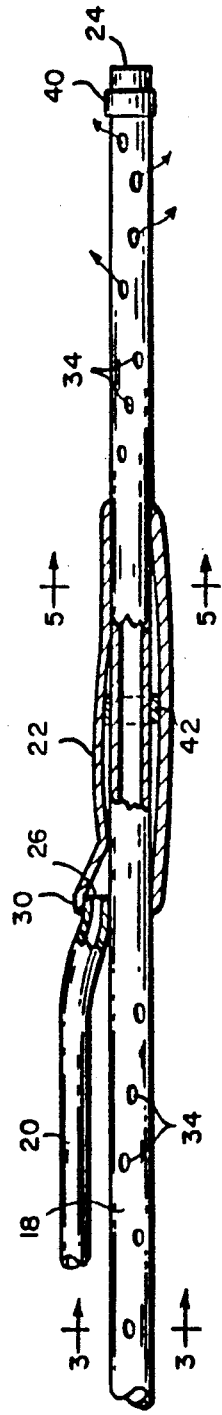
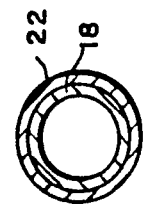
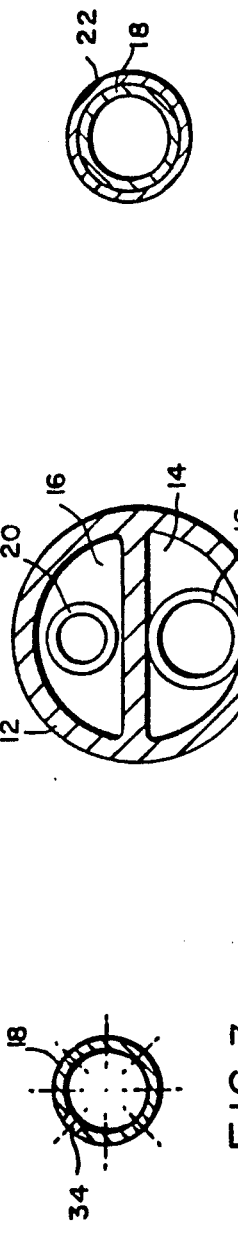
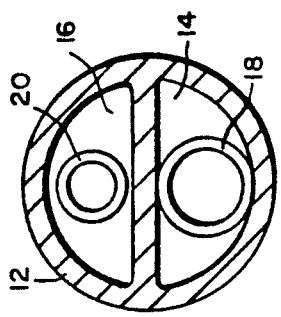

BALLOON PERFUSION CATHETER

FIELD OF THE INVENTION

This invention relates to perfusion catheters and, more particularly, to perfusion dilation catheters used for arterial angioplasty.

BACKGROUND OF THE INVENTION

Catheters are commonly used invasively to treat cardiovascular diseases through a method known as balloon angioplasty. A catheter is employed having a balloon portion near the catheter's distal end. The balloon portion is placed within an obstructed artery and inflated; expanding outwardly, the balloon dilates the arterial vessel.

Balloon angioplasty procedures when successful avoid bypass surgery and the attendant costs and medical risks thereof. Effective treatment of arterial stenoses, however, may not be realized through current balloon angioplasty methods for a number of reasons. For example, the lumen through the stenosis may be too narrow to permit entry of the deflated balloon catheter. Also, inflation times of currently used balloon catheters may be limited to 15 to 60 seconds due to occlusion of the arterial opening by the inflated balloon. This limited inflation time is often not sufficient to treat the stenosis and inflations must be repeated. Further, even if the arterial lumen is successfully dilated, the effect may be only temporary. Restenosis of the artery after treatment is not uncommon. It is believed, however, that a sustained inflation of the catheter balloon, rather than shorter multiple inflations, would reduce the possibility of such post-treatment restenosis.

A sustained inflation period also permits use of relatively lower inflation pressures. Extended, low pressure inflation tends to compress, rather than tear, plague of an arterial lesion over time. By not tearing the arterial lesion, healing of the dissection is facilitated. In contrast, conventional shorter multiple balloon inflations performed at relatively high inflation pressures could tear the arterial lesion thereby prolonging recovery or entirely preventing successful treatment.

SUMMARY OF THE INVENTION

The present invention comprises an improved balloon perfusion catheter that provides many advantages not afforded by conventional catheters. More specifically, the present invention provides a perfusion balloon catheter having a flexible elongated shaft, which shaft is provided with first and second lumens extending therewithin. A perfusion shaft and inflation shaft extend outwardly from, and are in communication with, the first and second lumens, respectively. A portion of the perfusion shaft has an angioplasty balloon mounted circumferentially therearound. The inflation shaft distal end is located at the balloon proximal end and therefore the inflation shaft does not enter the stenosis lumen during treatment. As the perfusion shaft with circumscribing balloon is the largest diameter portion of the catheter that need be inserted into an arterial stenosis, lesions having relatively small openings can be treated successfully.

Both proximal and distal to the balloon, the perfusion shaft has a plurality of openings which permit blood flow through the artery during balloon inflation thereby providing the advantage of longer balloon inflation time. Preferably, the openings spirally circumscribe the perfusion shaft both proximal and distal to the balloon, each opening being radially offset from each adjacent opening. Such spiral circumscription has been found to provide enhanced blood flow into and through the perfusion shaft.

The inflation shaft generally extends from the elongated shaft to the balloon at least partially separate from and without attachment to the perfusion shaft. At least partial separation of the perfusion shaft and inflation shaft permits advantageous circumscription of the perfusion shaft by the plurality of openings.

The perfusion shaft has a distal end radiopaque marker affixed thereon near the perfusion shaft distal end, a balloon radiopaque marker affixed thereon and beneath the balloon, and a proximal end radiopaque marker affixed thereon near the perfusion shaft proximal end. A guide wire may be inserted through the first lumen and the perfusion shaft to provide means for advancing the balloon to the targeted artery.

It is an object of the invention to provide a balloon dilation catheter which permits an angioplasty procedure on a stenosis lumen, including a narrow stenosis lumen.

It is another object of the invention to provide a balloon dilation catheter which affords enhanced blood perfusion through an obstructed artery during balloon inflation.

It is a further object of the invention to provide a balloon dilation catheter which permits use of relatively long balloon inflation times and low balloon inflation pressures.

BRIEF DESCRIPTION OF THE DRAWING

A more complete understanding of the invention may be provided by reference to the accompanying drawing wherein:

FIG. 1 is a top view of the catheter of the present invention;

FIG. 2 is an enlarged top view of a distal portion of the catheter of the present invention;

FIG. 3 is a cross-sectional view taken along the line 3—3 of FIG. 2;

FIG. 4 is a cross sectional view taken along the line 4—4 of FIG. 1.; and

FIG. 5 is a cross-sectional view taken along the line 5—5 of FIG. 2.

DESCRIPTION OF THE PREFERRED EMBODIMENT

The present invention as shown in FIGS. 1-5 provides a catheter 10 having a flexible elongated shaft 12 with first lumen 14 longitudinally extending therewithin and second lumen 6 longitudinally extending therewithin. Perfusion shaft 18 extends outwardly from, and communicates with, first lumen 14. First lumen 14 and perfusion shaft 18 are adapted to receive a guide wire (not shown). The guide wire enables directing catheter 10 to the targeted arterial stenosis through manipulation at the catheter's proximal end 19. Inflation shaft 20 outwardly extends from, and communicates with, second lumen 16. First lumen 14 is adapted to receive perfusion shaft 18, and second lumen 16 is adapted to receive inflation shaft 20. In general, lumen 14 is between about 0.014 and 0.022 inches in diameter and lumen 16 is between about 0.010 and 0.016 inches in diameter, and preferably lumen 14 is about 0.020 inches in diameter and lumen 16 is about 0.014 inches in diameter. Generally, perfusion shaft 18 is between about 0.030 and 0.040 inches in diameter and inflation shaft 20 is between, 0.013 and 0.026 inches in diameter, and preferably shaft 18 is about 0.039 inches in diameter and shaft 18 is about 0.018 inches in diameter. It should be made clear, however, that the diameter of perfusion shaft 18 may vary with a number of factors, for example a patient's blood pressure.

As apparent to those skilled in the art, the length of catheter 10 and shafts 12, 18 and 20 will vary with arterial location and patient characteristics. In one preferred embodiment of the catheter as adapted for coronary treatment, catheter 10 is about 145 cm. in length, shaft 12 is about 135 cm. in length, and perfusion shaft 18 is about 10 cm. in length.

Perfusion shaft 18 is circumscribed by inflatable balloon 22 and extends beyond balloon 22 to perfusion shaft distal end 24. Perfusion shaft 18 may extend between about 1 and 10 cm. beyond the balloon to distal end 24, and preferably extends between about 2 and 4 cm. beyond balloon 22 to distal end 24. Inflation shaft 20 communicates with balloon 22 at inflation shaft distal end 26 and at balloon proximal end 30, as clearly shown in FIG. 2.

Because inflation shaft 20 terminates at the balloon's proximal end 30, perfusion shaft 18 with circumscribing balloon 22 is of a significantly smaller diameter than in prior systems where the inflation shaft terminates further within the balloon, beyond the balloon proximal end. As perfusion shaft 18 with circumscribing balloon 22 is the largest diameter portion of catheter 10 that need be inserted into an arterial stenosis opening, stenoses having relatively narrow lumens may be successfully treated. Current perfusion balloon angioplasty treatment of such narrow lumen stenoses is not possible through use of conventional perfusion balloon catheters that have too large a diameter to permit stenoric insertion.

Inlet 32 communicates with second lumen 16 and thus in turn inflation shaft 20. Fluid is introduced and discharged through inlet 32 to inflate and deflate balloon 22.

Perfusion shaft 18 may extend from elongated shaft 12 to perfusion shaft distal end 24 at least partially separate from and without attachment to inflation shaft 20. In general, perfusion shaft 18 extends to perfusion shaft distal end 24 separate and without attachment to inflation shaft 20 for at least about ten percent of the length of perfusion shaft 18, and preferably perfusion shaft 18 extends from elongated shaft 12 separate from and without attachment to inflation shaft 20, and then attaches to inflation shaft 20 at inflation shaft distal end 26.

Perfusion shaft 18 has plurality of openings 34 extending therethrough both proximal and distal to balloon 22. Openings 34 provide a path for blood flow through first carrier shaft 18 during inflation of balloon 22. Blood perfuses through openings 34 proximate to balloon 22, flows through perfusion shaft 18, and then flows out of catheter 10 through openings 34 distal to balloon 22 and through perfusion shaft distal end 24. By providing blood flow through the artery during balloon inflation, long inflation times at relatively lower inflation pressures can be employed affording the noted advantages thereof.

Preferably, plurality of openings 34 circumscribe perfusion shaft 18 both proximal and distal to balloon 22. Each opening 34 may be positioned relative to each adjacent opening 34 by a variety of geometries. It is preferred, however, to radially offset each opening 34 from each adjacent opening so that openings 34 spirally circumscribe perfusion shaft 18, as shown in FIG. 3, and, most preferably, each opening is radially offset from each adjacent opening by a forty-five degree angle. Radially offsetting openings 34 has been found to provide particularly enhanced blood perfusion into and through shaft 18.

The spiral circumscription of shaft 18 by openings 34 helps to prevent problems encountered with previous catheters. In previous catheters, the perfusion shaft openings, if present at all, are typically positioned only on one side of the perfusion shaft. When that shaft side contacts an arterial surface or is otherwise obstructed, blood flow into the shaft will be blocked, preventing blood perfusion through the artery during balloon inflation. Circumscription of perfusion shaft 18 by openings 34 as in the present invention ensures that even if blood flow is impeded to portions of perfusion shaft 18, blood may freely flow through openings positioned on other shaft portions.

It should be noted that circumscription of shaft 18 by openings 34, and the advantages thereof, are preferably achieved by shafts 18 and 20 comprising two largely separate and unattached tubes. If the two shafts were attached to comprise a single composite shaft, to maintain the necessary separation of inflation fluid and blood, either the perfusion openings could not circumscribe the composite shaft or a much more cumbersome and less advantageous system than the present invention would be required.

Distal end marker 40 is affixed to perfusion shaft 18 near perfusion shaft distal end 24. Balloon marker 42 is affixed to perfusion shaft 18 beneath balloon 22, preferably beneath the center of the balloon. Proximal end marker 44 is affixed to perfusion shaft 18 near perfusion shaft proximal end 38.

Markers 40, 42 and 44 are preferably composed of gold or platinum or other radiopaque material and are attached to carrier shaft 18 by crimping. Markers 40, 42 and 44 are fluoroscopically visible and aid in directing catheter 10 to, and centering balloon 22 in, the diseased area of an artery.

Plurality of openings 34 preferably extend from perfusion shaft proximal end 38 to balloon 22, and then from balloon 22 to distal end marker 40. Openings 34 may be a variety of geometries in shape and are preferably round. In general, openings 34 are between about 0.010 and 0.040 inches in diameter, preferably between about 0.014 and 0.024 inches in diameter, and most preferably about 0.022 inches in diameter. In general, the number of openings proximal to balloon 22 may be about 4 to 40, preferably about 10 to 40, and most preferably about 20 to 30. In general, the number of openings distal to balloon 22 may be about 2 to 20, preferably about 4 to 10, and most preferably 6 to 8.

The dual-lumen shaft 12, perfusion shaft 18 and inflation shaft 20 are preferably formed separately through a polymer extrusion process. In one preferred embodiment, first lumen 14 is attached to perfusion shaft 18, and second lumen 16 is attached to inflation shaft 20, by means of a suitable adhesive or heat bonding. Balloon 22 is attached to perfusion shaft 18 by an adhesive or heat bonding. Plurality of openings 34 are cut or drilled through perfusion shaft 18. Heat bonding is the preferred means of attaching inflation shaft distal end 26 to shaft 18.

As with previous catheters, the catheter of the present invention is inserted into a patient and advanced to the area of treatment by means of the guide wire and markers 40, 42 and 44. Prior to insertion into the patient or to positioning within the lesion lumen, balloon 22 is prepared for use by introducing a pressurized fluid through inlet 32 thereby displacing trapped air from balloon 22, inflation shaft 20 and second lumen 16. A negative pressure is then applied to withdraw the fluid and deflate the balloon. Thereafter, balloon 22 is inflated and deflated as desired.

The foregoing description of the present invention is merely illustrative thereof, and it is understood that variations and modifications can be effected without departing from the spirit or scope of the invention as set forth in the following claims.

We claim:
1. A dilation catheter, comprising:
 (a) a flexible elongated shaft having a first lumen longitudinally extending therewithin and a second lumen longitudinally extending therewithin;
 (b) a perfusion shaft outwardly extending from and in communication with the first lumen;
 (c) a balloon circumscribing the perfusion shaft, the perfusion shaft having a plurality of openings proximal and distal to the balloon; and
 (d) an inflation shaft outwardly extending from and in communication with the second lumen, the perfusion shaft for at least a portion of its length being physically separate from the inflation shaft.

2. A dilation catheter as recited in claim 1, wherein the plurality of openings are offset to at least partially circumscribe the perfusion shaft both proximal and distal to the balloon.

3. A dilation catheter as recited in claim 1, wherein the plurality of openings spirally circumscribe the perfusion catheter both proximal and distal to the balloon.

4. A dilation catheter as recited in claim 1, wherein the perfusion shaft extends from the flexible elongated shaft separate from and without attachment to the inflation shaft, and then attaches to the inflation shaft at the inflation shaft distal end.

5. A dilation catheter as recited in claim 1, wherein the perfusion shaft extends to the perfusion shaft distal end separate from and without attachment to the inflation shaft for at least about 10 percent of the length of the perfusion shaft.

6. A dilation catheter as recited in claim 1, wherein the first lumen and the perfusion shaft are adapted to receive a guide wire.

7. A dilation catheter as recited in claim 1, wherein the second lumen and the inflation shaft are adapted to receive fluid.

8. A dilation catheter as recited in claim 1, wherein a distal end marker is affixed on the perfusion shaft near the perfusion shaft distal end, a balloon marker is affixed on the perfusion shaft beneath the balloon, and a proximal end marker is affixed on the perfusion shaft near the perfusion shaft proximal end.

9. A dilation catheter as recited in claim 1, wherein there are between about 4 to 40 openings proximal to the balloon and between about 2 to 20 openings distal to the balloon.

10. A dilation catheter as recited in claim 1, wherein there are between about 10 and 40 openings proximal to the balloon and between about 4 and 10 openings distal to the balloon.

11. A dilation catheter as recited in claim 1, wherein there are between about 20 to 30 openings proximal to the balloon and between about 6 to 8 openings distal to the balloon.

12. A dilation catheter as recited in claim 1, wherein the plurality of openings are round in shape.

13. A dilation catheter as recited in claim 1, wherein each opening is between about 0.010 and 0.040 inches in diameter.

14. A dilation catheter as recited in claim 1, wherein each opening is between about 0.014 nd 0.024 inches in diameter.

15. A dilation catheter as recited in claim 1, wherein each opening is about 0.022 inches in diameter.

16. A dilation catheter as recited in claim 1, wherein the inflation shaft communicates with the balloon at the inflation shaft distal end and the balloon proximal end.

17. A dilation catheter as recited in claim 1, wherein the plurality of openings circumscribe the perfusion shaft both proximal and distal to the balloon.

* * * * *